US009643902B2

(12) United States Patent
Mathys et al.

(10) Patent No.: US 9,643,902 B2
(45) Date of Patent: May 9, 2017

(54) PROCESSES UTILIZING SOLVENT EXTRACTION

(75) Inventors: Georges M. K. Mathys, Bierbeek (BE); Marc P. H. Puttemans, Schepdaal (BE); Geraldine Tosin, Woluwe Saint Lambert (BE); Eddy T. Van Driessche, Eeklo (BE); Paul Hamilton, Eastleigh (GB); Marcel J. G. Janssen, Leuven (BE)

(73) Assignee: ExxonMobil Chemical Patents Inc., Baytown, TX (US)

( * ) Notice: Subject to any disclaimer, the term of this patent is extended or adjusted under 35 U.S.C. 154(b) by 494 days.

(21) Appl. No.: 13/885,972

(22) PCT Filed: Aug. 31, 2011

(86) PCT No.: PCT/US2011/049988
§ 371 (c)(1),
(2), (4) Date: Aug. 7, 2013

(87) PCT Pub. No.: WO2012/078218
PCT Pub. Date: Jun. 14, 2012

(65) Prior Publication Data
US 2014/0148625 A1      May 29, 2014

Related U.S. Application Data

(60) Provisional application No. 61/420,602, filed on Dec. 7, 2010.

(30) Foreign Application Priority Data

Feb. 1, 2011  (EP) ..................................... 11152926

(51) Int. Cl.
| | | |
|---|---|---|
| C07C 7/10 | (2006.01) | |
| C07C 2/24 | (2006.01) | |
| C10G 21/06 | (2006.01) | |
| C10G 21/16 | (2006.01) | |
| C10G 21/26 | (2006.01) | |
| C10G 50/00 | (2006.01) | |

(52) U.S. Cl.
CPC .................. *C07C 7/10* (2013.01); *C07C 2/24* (2013.01); *C10G 21/06* (2013.01); *C10G 21/16* (2013.01); *C10G 21/26* (2013.01); *C10G 50/00* (2013.01); *C10G 2300/1081* (2013.01); *C10G 2300/1088* (2013.01); *C10G 2300/202* (2013.01); *C10G 2300/308* (2013.01); *C10G 2300/44* (2013.01); *C10G 2400/22* (2013.01)

(58) Field of Classification Search
CPC ..... C07C 7/10; C07C 2/24; C10G 2300/1088; C10G 50/00; C10G 2300/44; C10G 2400/22; C10G 2300/202; C10G 2300/308; C10G 2300/1081; C10G 21/16; C10G 21/06; C10G 21/26

USPC ....... 585/251, 254, 865, 857, 329, 518, 833, 585/862, 866, 820
See application file for complete search history.

(56) References Cited

U.S. PATENT DOCUMENTS

| | | | |
|---|---|---|---|
| 4,153,638 A | | 5/1979 | Bercik et al. |
| 4,374,732 A | * | 2/1983 | Hopper .................. B01D 15/00 210/690 |
| 4,973,790 A | | 11/1990 | Beech et al. |
| 5,446,231 A | * | 8/1995 | Arganbright .............. C07C 7/10 585/802 |
| 5,675,043 A | * | 10/1997 | Eppig ..................... C10G 21/00 568/697 |
| 5,834,392 A | | 11/1998 | Ramirez de Agudelo et al. |
| 5,858,211 A | | 1/1999 | Ramirez de Agudelo et al. |
| 5,880,052 A | | 3/1999 | Ramirez de Agudelo et al. |
| 6,019,887 A | | 2/2000 | Ramirez de Agudelo et al. |
| 6,160,193 A | | 12/2000 | Gore |
| 7,205,448 B2 | | 4/2007 | Gajda et al. |
| 7,389,639 B2 | * | 6/2008 | Michalakos ........... B01D 53/75 210/669 |
| 7,744,828 B2 | | 6/2010 | Schmidt et al. |
| 2002/0103406 A1 | | 8/2002 | Mathys et al. |
| 2004/0097773 A1 | * | 5/2004 | Beckmann ................ C07C 2/28 585/530 |
| 2006/0088461 A1 | * | 4/2006 | Shuki ..................... B01D 53/14 423/238 |
| 2007/0213575 A1 | * | 9/2007 | Godsmark ................ C07C 2/12 585/518 |
| 2008/0312484 A1 | | 12/2008 | Godsmark et al. |

FOREIGN PATENT DOCUMENTS

| | | |
|---|---|---|
| GB | 1131989 | 10/1968 |
| SU | 1086006 A | 4/1984 |
| WO | WO 00/71494 | 11/2000 |
| WO | WO 03080225 A1 * | 10/2003 ............. B01D 61/00 |

OTHER PUBLICATIONS

Zaretskii, M. I.; Rusak, V. V.; Chartov, E. M. "Using Propylene Carbonate in Extraction and Absorption: A Review" Coke and Chemistry (2008), vol. 51, No. 3, pp. 101-104.*
"Solvent Extraction Principles and Practice", 2nd edition; Rydberg, J.; Cox, M.; Musikas, C.; Choppin, G., Eds.: Marcel Dekker, Inc.: New York, 2008; pp. 12-13.*
Nagai et al., *Isolation of Nitrogen-containing Heterocyclic Compounds Contained in Coal Tar Absorption Oil Fraction With Solvent Extraction*, Sekiyu Gakkaishi (Journal of the Japan Petroleum Institute), 43 (5), pp. 339-345, (2000) (translation).

* cited by examiner

*Primary Examiner* — In Suk Bullock
*Assistant Examiner* — Aaron Pierpont
(74) *Attorney, Agent, or Firm* — Darryl M. Tyus

(57) ABSTRACT

Embodiments of an invention disclosed herein relate to processes utilizing solvent extraction to remove nitrogen containing compounds and optionally other components from feedstreams of olefins and paraffins.

25 Claims, No Drawings

PROCESSES UTILIZING SOLVENT EXTRACTION

CROSS-REFERENCE TO RELATED APPLICATIONS

This application is a 371 National Stage Application of International Application No. PCT/US2011/049988, filed Aug. 31, 2011, which claims the benefit of U.S. Ser. No. 61/420,602, filed Dec. 7, 2010, and EP Application No. 11152926.9, filed Feb. 1, 2011, the disclosures of which are incorporated herein by reference in their entireties.

FIELD OF THE INVENTION

Embodiments disclosed herein relate to processes utilizing solvent extraction to remove nitrogen containing compounds and optionally other components from feedstreams of olefins and paraffins.

BACKGROUND

The condensation reaction of an olefin or a mixture of olefins to form higher molecular weight products is widely known and practiced. This type of condensation reaction is referred to herein as an oligomerization reaction, and the products are low molecular weight oligomers which are formed by the condensation of up to 12, typically 2, 3 or 4, but up to 5, 6, 7, or even 8 olefin molecules with each other. "Oligomerization" refers to a process for the formation of oligomers and/or polymers. Low molecular weight olefins (such as, for example, ethylene, propene, 2-methylpropene, 1-butene and 2-butenes, pentenes and hexenes) may be converted by oligomerization over, for example, a solid phosphoric acid catalyst (commonly referred to as "sPa" catalyst) or a molecular sieve catalyst (e.g., a zeolite catalyst), to an oligomer product.

Oligomer products are valuable components of high-octane gasoline blending stock that may be used or blended into a distillate type liquid fuel or as a lubricant, or as a starting material for the production of chemical intermediates and end-products. Such chemical intermediates and end-products include high purity hydrocarbon fluids or solvents, alcohols, detergents/surfactants, and esters such as plasticizer esters and synthetic lubricants.

A number of catalysts may be used in such oligomerization processes. For example, industrial oligomerization reactions employing molecular sieve catalysts are generally performed in a plurality of tubular or chamber reactors, similar to those processes employing sPa catalysts. With sPa catalysts, the pressure drop over the catalyst bed(s) increases gradually over the duration of the run, due to coking and/or swelling of the catalyst pellets and the reactor run is typically terminated when a maximum allowable pressure drop over the reactor is reached. Molecular sieve catalysts do not show pressure drop increases similar to sPa catalysts. Oligomerization reactors using molecular sieve catalysts are therefore characterized by longer reactor run lengths and are typically decommissioned when the catalyst activity has dropped to an unacceptably low level. With these catalysts, the reactor run length that can be achieved is therefore much more sensitive to compounds, impurities, or contaminants in the feedstreams that deactivate the catalyst, such as catalyst poisons.

Strong bases, such as the proton bases or Bronsted bases, are known poisons for many of the oligomerization catalysts that are acidic, for example, molecular sieve catalysts. Such bases in hydrocarbon streams are often nitrogen containing compounds, such as amines, amides, and/or nitriles, and they are typically removed from feedstreams for oligomerization reactions and other hydroprocessing reactions. Such organic nitrogen-containing Bronsted bases are characterized by at least one hydrogen atom bound to the nitrogen atom and are known proton acceptors. Other organic nitrogen components do not have any hydrogen atoms bound to the nitrogen and the nitrogen atom may have three bonds to 1, 2 or 3 surrounding carbon atoms. These nitrogen atoms however still have a free electron pair and therefore can still act as a base, termed a Lewis base. Lewis bases are known to be weaker bases as compared to Bronsted bases and therefore are sometimes considered less problematic to acid catalyzed processes. The past is replete with attempts to treat feedstreams prior to undergoing any hydroprocessing reaction.

For example, U.S. Pat. No. 4,973,790 discloses a process for oligomerization of $C_2$ to $C_{10}$ olefins over a zeolite catalyst comprising a feed pre-treatment step to remove basic nitrogen compounds. It is directed to the removal of amines such as di-ethanol-amine.

U.S. Pat. No. 4,153,638 discloses a process for polymerizing $C_2$ to $C_5$ olefins to form gasoline and distillate boiling range oligomer products in the presence of a metal-substituted synthetic mica montmorillonite catalyst.

U.S. Patent Application Publication No. 2002/103406 discloses a process for oligomerizing an olefin originating from an oxygenate to olefin process using a nickel based catalyst. The olefin stream has a low nitrogen content, as low as 0.3 ppm by weight. This stream is therefore very suitable for oligomerization using nickel based catalysts because these catalysts are known to be particularly sensitive to poisons, such as nitrogen compounds.

U.S. Patent Application Publication No. 2004/0097773 discloses a process for oligomerizing isobutene. It discloses the removal of nitrogen components from the feed stream including acetonitrile and N-methyl-pyrrolidone. Both compounds are nitrogen-containing Lewis bases. The catalyst used in U.S. Patent Application Publication No. 2004/0097773 is a solid, acidic ion exchange resin in which some of the acidic protons have been exchanged for a metal ion.

U.S. Pat. Nos. 7,205,448, 7,744,828, and U.S. Patent Application Publication No. 2007/0213575 disclose the removal of nitrogen compounds, including a number of Lewis base compounds such as acetonitrile, N-methyl-pyrrolidone, morpholines such as N-formyl morpholine, pyridine and/or quinoline, from feedstreams.

Other background references include U.S. Patent Application Publication Nos. 2005/0137442, 2005/0152819, 2008/0312484, U.S. Pat. No. 6,160,193, GB 1,131,989, and WO 2000/71494. Thus, many catalysts and their respective catalyst lives may be profoundly influenced by contaminants, such as, for example, nitrogen containing compounds (e.g., nitriles) and other contaminants such as for example, sulfur containing compounds, in feedstreams. Therefore, there remains a long-standing need to address the problems associated with basic contaminants in feedstreams.

In response, solvent extraction processes have been used in the past to treat certain feedstreams. For example, U.S. Pat. No. 5,675,043 discloses processes for treating a hydrocarbon blend containing nitrogen-containing compounds with a solvent having a Hansen polar solubility parameter to effect removal of a portion of said nitrogen-containing compounds therefrom. (See claim 1). Example 1 exemplifies the use of sulfolane. Nagai et al., *Isolation of Nitrogen-containing Heterocyclic Compounds Contained in Coal Tar*

Absorption Oil Fraction with Solvent Extraction, Sekiyu Gakkaishi (Journal of the Japan Petroleum Institute), 43 (5), 339-345 (2000), discloses using aqueous solutions of methanol or tetrahydrothiophene-1,1-dioxide (sulfolane) to remove heterocyclic compounds containing nitrogen atoms from coal tar oil absorption oil fractions. In other areas, SU 1086006 discloses using a metal chloride such as $NiCl_2$ in an organic solvent such as propylene carbonate or dimethylsulfoxide or dimethylformamide to remove nitrogen compounds from petroleum products by complexing the metal chloride with the nitrogen compounds. Despite these past endeavors, there remains a need to improve upon the removal of nitrogen containing compounds, such as, for example, one or more nitriles and optionally other components, from feedstreams of olefins and paraffins to allow for downstream processing such as hydroprocessing to occur more efficiently.

SUMMARY

In a class of embodiments, the invention provides for a process for removing nitriles and/or pyrroles from a feedstream, the process comprising:

contacting at least one feedstream comprising olefins, paraffins, and at least one of a nitrile and a pyrrole with at least one solvent and removing at least a portion of the nitrile and the pyrrole from the at least one feedstream;

wherein the process comprises a distribution coefficient expressed by the following:

$$(D) = \frac{molNP/l_{fs}}{molNP/l_{sol}}$$

wherein $molNP/l_{fs}$ is the molar concentration of the nitrile and the pyrrole in the feedstream after extraction; $molNP/l_{sol}$ is the molar concentration of the nitrile and the pyrrole in the solvent(s) after extraction; and (D) is from 0.04 to 0.50;

wherein the at least one feedstream has a liquid density (in accordance with ASTM D4052) at 15° C. of 0.94 kg/l or less; and wherein the at least one feedstream comprises at least 3.00 ppm nitrogen derived from the nitrile and/or the pyrrole before the contacting and the at least one feedstream comprises 1.50 ppm or less of nitrogen derived from the nitrile and/or the pyrrole after contacting the at least one feedstream with the at least one solvent.

In another class of embodiments, the invention provides for a process for the oligomerization of olefins, the process comprising:

contacting at least one feedstream comprising olefins, paraffins, and at least one of a nitrile and a pyrrole with at least one solvent and removing at least a portion of the nitrile and the pyrrole from the at least one feedstream to produce at least one treated feedstream, and subsequently contacting the at least one treated feedstream with a catalyst under oligomerization conditions to produce oligomers;

wherein the process comprises a distribution coefficient expressed by the following:

$$(D) = \frac{molNP/l_{fs}}{molNP/l_{sol}}$$

wherein $molNP/l_{fs}$ is the molar concentration of the nitrile and the pyrrole in the feedstream after extraction; $molNP/l_{sol}$ is the molar concentration of the nitrile and the pyrrole in the solvent after extraction; and (D) is from 0.04 to 0.50;

wherein the at least one feedstream has a liquid density (in accordance with ASTM D4052) at 15° C. of 0.94 kg/l or less; and wherein the at least one feedstream comprises at least 3.00 ppm nitrogen derived from the nitrile and/or the pyrrole before the contacting and the at least one treated feedstream comprises 1.50 ppm or less of nitrogen derived from the nitrile and/or the pyrrole after contacting the at least one feedstream with the at least one solvent.

In any of the embodiments described herein, the at least one feedstream may comprise 1.00 ppm or less of nitrogen after contacting the at least one feedstream with the at least one solvent.

In any of the embodiments described herein, the at least one feedstream may comprise 0.50 ppm or less of nitrogen after contacting the at least one feedstream with the at least one solvent.

In any of the embodiments described herein, the at least one feedstream may comprise 0.30 ppm or less of nitrogen after contacting the at least one feedstream with the at least one solvent.

In any of the embodiments described herein, the at least one feedstream may comprise 0.10 ppm or less of nitrogen after contacting the at least one feedstream with the at least one solvent.

DETAILED DESCRIPTION

Before the present compounds, components, compositions, and/or methods are disclosed and described, it is to be understood that unless otherwise indicated this invention is not limited to specific compounds, components, compositions, reactants, reaction conditions, or the like, as such may vary, unless otherwise specified. It is also to be understood that the terminology used herein is for the purpose of describing particular embodiments only and is not intended to be limiting.

It must also be noted that, as used in the specification and the appended claims, the singular forms "a," "an," and "the" include plural referents unless otherwise specified.

In several classes of embodiments, the invention provides for processes utilizing solvent extraction to remove nitrogen containing compounds, for example, one or more nitriles, and optionally other components from mixed olefin feedstreams of olefins and paraffins. Following, those treated feedstreams may be used in oligomerization processes having, for example, desirable catalyst life. In some embodiments, the invention also provides for the regeneration and recycle of the solvents after being utilized in the extraction processes.

Solvent Extraction

Solvent extraction also referred to as liquid-liquid extraction and partitioning is a method to separate compounds based on their relative solubilities, for example, in at least two immiscible liquids or phases. It generally proceeds as an extraction of a substance from one liquid phase into another liquid phase wherein each liquid phase may comprise the same or different solvent(s). In particular, it generally attempts to separate a substance from a mixture by dissolving that substance in a suitable solvent and removing the substance and solvent from the mixture. The mixture may then proceed to further processing to produce desired end-products. Liquid-liquid extraction is a basic chemical technique and may be applied from a smaller scale in laboratories using, for example, a respiratory funnel, to an industrial scale using, for example, large separation towers.

Distribution Ratio

In a class of embodiments, a distribution ratio or distribution coefficient (D) may be used to measure the efficiency of an extracted species or compound. The distribution ratio or distribution coefficient (D) is equal to the concentration of a solute in a first phase (gr/gr or moles/liter) divided by its concentration in a second phase (gr/gr or mole/liter). Depending on the system, the distribution ratio may be a function of temperature, pressure, the concentration of compounds in the system, and other parameters.

In several embodiments related to nitriles and pyrroles, the distribution coefficient may be expressed by the following:

$$(D) = \frac{molNP/l_{fs}}{molNP/l_{sol}}$$

wherein $molNP/l_{fs}$ is the molar concentration of the nitrile and the pyrrole in the feedstream after extraction; $molNP/l_{sol}$ is the molar concentration of the nitrile and the pyrrole in the solvent(s) after extraction. In an embodiment, (D) is from 0.04 to 0.50. In other embodiments, (D) is from 0.04 to 0.10, alternatively, from 0.04 to 0.08, and alternatively, (D) may be about 0.05.

In an embodiment, the distribution coefficient may be expressed by the following:

$$(D) = \frac{molPCN/l_{C5+}}{molPCN/l_{PC}}$$

wherein $molPCN/l_{C5}$ is the molar concentration of nitriles, for example, propionitrile, in a $C_5$ sample after extraction and $molPCN/l_{PC}$ is the molar concentration of nitriles, for example, propionitrile, in propylene carbonate after extraction. In an embodiment, (D) is from 0.04 to 0.50. In other embodiments, (D) is from 0.04 to 0.10, alternatively, from 0.04 to 0.08, and alternatively, (D) may be about 0.05.

In yet another embodiment, the distribution coefficient may be expressed by the following:

$$(D) = \frac{molPCN/l_{C5+}}{molPCN/l_{PSulf}}$$

wherein $molPCN/l_{C5}$ is the molar concentration of nitriles, for example, propionitrile, in a $C_5$ sample after extraction and $molPCN/lP_{PSulf}$ is the molar concentration of nitriles, for example, propionitrile, in sulfolane after extraction. In an embodiment, (D) is from 0.04 to 0.50. In other embodiments, (D) is from 0.04 to 0.10, alternatively, from 0.04 to 0.08, and alternatively, (D) may be about 0.05.

In several classes of embodiments, the extraction process or contacting at least one feedstream with at least one solvent may be performed in the temperature range of from −40° C. to 100° C., alternatively, from −25° C. to 75° C., alternatively, from −30° C. to 75° C., alternatively, from −25° C. to 60° C., and alternatively, from −15° C. to 50° C. In a class of embodiments, extraction processes may occur at ambient or sub ambient temperatures. In several embodiments, the pressure should be at least high enough to keep both phases in essentially the liquid state to facilitate separation of the two phases.

The extraction process may be executed in the co-current mode, in which the immiscible liquids (i.e., at least one feedstream and at least one solvent) flow in the same direction. Alternatively, the extraction process may be executed in the counter-current mode, where the immiscible liquids (i.e., at least one feedstream and at least one solvent) flow in opposite directions.

Solvents

Sulfones

The solvent extraction processes employ at least one solvent. In several classes of embodiments, the at least one solvent comprises, consists essentially of, consists of, or may be sulfone or one or more sulfone compounds. As used herein, "sulfone" or "sulfone compounds" refers to a group of organosulfur compounds containing a sulfonyl functional group. The sulfonyl group is a sulfur atom doubly bonded to two oxygen atoms. The sulfur-oxygen double bond is highly polar, allowing for its high solubility in water, while the four carbon ring provides non-polar stability. In a class of embodiments, the at least one solvent comprises sulfolane (also known as tetramethylene sulfone and 2,3,4,5-tetrahydrothiophene-1,1-dioxide). It is a clear, colorless liquid. Sulfolane is an aprotic organosulfur solvent, i.e., a solvent that neither accepts nor donates protons. It may be represented by the following structure.

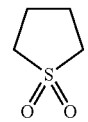

Sulfolane is highly stable and may be reused with some treatment but eventually breaks down into acidic byproducts as well as contain process contaminants. Methods have been developed to remove these byproducts and contaminants including but not limited to vacuum and steam distillation, back extraction, adsorption, and anion-cation exchange resin columns. Regeneration and recycle are discussed in more detail below.

Carbonates

In another class of embodiments, the at least one solvent comprises, consists essentially of, consists of, or may be one or more of an alkyl/alkenyl/aryl carbonate. As used herein, "alkyl" refers to a hydrocarbon group which may be derived from an alkane by dropping one or more hydrogens from the alkane, such as, for example, a methyl group, an ethyl group, a propyl group, etc. As used herein, "alkenyl" refers to an unsaturated hydrocarbon group containing one ore more pairs of carbon atoms linked by a double bond. Examples include an ethylene group, a propylene group, etc. As used herein, "aryl" refers to a hydrocarbon group that forms a ring structure characteristic of aromatic compounds such as, for example, benzene, naphthalene, phenanthrene, anthracene, etc., and typically possess alternate double bonding within its structure. An aryl group is thus a group derived from an aromatic compound by dropping one or more hydrogens from the aromatic compound such as, for example, phenyl group, etc. As used herein, "hydrocarbon" or "hydrocarbon group" refers to compounds or a group of molecules consisting essentially of hydrogen and carbon. The hydrocarbon or hydrocarbon group may be cyclic, linear, branched, substituted, etc.

The at least one solvent may comprise one or more, independently the same or different, of the alkyl/alkenyl/aryl carbonates as described above and, optionally, other solvents.

In a class of embodiments, the at least one solvent comprises propylene carbonate ("PC"). Propylene carbonate is an organic compound and may be a twofold ester of propylene glycol and carbonic acid. It is a colorless and odorless liquid. Propylene carbonate is a highly polar and aprotic solvent. It may be represented by the following structure.

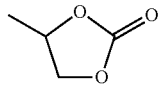

In other embodiments, the at least one solvent may comprise glycols and/or water. Suitable glycols may include any organic alcohol compound that comprises at least two hydroxyl groups (OH) attached to different carbon atoms. Exemplary molecules may include ethylene glycol(1,2-ethanediol), tri-ethylene glycol(2-[2-(2-hydroxyethoxy)ethoxy] ethanol), propylene glycol(1,2-propanediol), 1,3-butanediol, 1,4-butanediol, 2-ethyl-1,3-hexanediol, 2-methyl-2-propyl-1,3-propanediol, and mixtures thereof.

Commercial grades of the at least one solvent may comprise contaminants such as nitrogen, sulfur containing species etc. In order to develop an efficient process, ideally these contaminants should be removed prior to utilizing in the extraction process. Commercial grades of solvents may be contacted with one or more adsorbents including without limitation molecular sieves, activated carbons, silicagels, resins (e.g., acid resins), and mixtures thereof.

Specific examples include without limitation molecular sieve 3A (activated 16 h @ 200° C. & vac), molecular sieve 13X (activated 1 h @ 200° C. & vac), Cameron SG6 carbon (12*40 mesh, coconut shell based BCT 4443), Cameron SG6 carbon (8*30 mesh, coconut shell based, BCT 4444), Norit GAC 830W 640316, BCT 4475 active coal, Keiselgel Fein silicagel (MN), Amberlyst 15 A, and silica bound ex fr F103runE60.

The at least one solvent as described above may comprise, in any proportion, one or more of the solvents as described above including other suitable solvents not described herein.

For certain embodiments, the process, the at least one solvent, or the feedstream(s) does not comprise a metal chloride. In any of the embodiments described herein, the alkyl/alkenyl/aryl carbonates do not comprise a complex such as a metal complex.

In some embodiments, the process proceeds with the proviso that the at least one solvent does not comprise sulfolane.

Feedstreams and Oligomerization Processes

The at least one feedstream comprises olefins and paraffins. In a class of embodiments, the at least one feedstream comprises olefins having from about 2 to about 15 carbon atoms, such as, for example, from about 3 to about 6 carbon atoms and one or more paraffins. As used herein, "olefins" refers to any of the unsaturated hydrocarbons ("hydrocarbon" as defined above) having the formula $C_nH_{2n}$, wherein C is a carbon atom, H is a hydrogen atom, and n is an integer from 1 to 25, typically, from 1 to 15, alternatively, from 3 to 6. As used herein, "paraffins" refers to any of the saturated hydrocarbons ("hydrocarbon" as defined above) having the formula $C_nH_{2n+2}$, wherein C is a carbon atom, H is a hydrogen atom, and n is an integer from 1 to 25, typically, from 1 to 15, alternatively, from 3 to 6. Additionally, in several embodiments, the feedstream may comprise an oligomer, such as, for example, a dimer, especially one provided by recycling a part of a product stream.

The feedstream may comprise olefins and paraffins having the same or different number of carbon atoms.

In a class of embodiments, the feedstream comprises one or more of propene, butenes, pentenes, hexenes, their isomers, and mixtures thereof. The process is especially useful for the oligomerization of feedstreams comprising propene, butenes, pentenes, their isomers, other components, and mixtures thereof.

As used herein, "oligomer(s)" or "oligomer product" refers to a polymer molecule (or a mixture of polymer molecules) made from a few monomer units such as, for example, a dimer, a trimer, a tetramer, a mixture thereof, etc. In a class of embodiments, "oligomer(s)" refers to a polymer molecule (or a mixture of polymer molecules) having 20 carbon atoms or less, alternatively, 15 carbon atoms or less, alternatively, 10 carbon atoms or less, alternatively, 9 carbon atoms or less, and alternatively, 8 carbon atoms or less. As used herein, "oligomerization process" refers to any process of catalytically joining monomer units to form the oligomer(s) as defined above. In a class of embodiments, oligomerization process is used synonymously with "polymerization process." As used herein, the term "oligomerization conditions" refers to any and all those variations of equipment, conditions (e.g., temperatures, pressures, etc.), materials, and reactor schemes that are suitable to conduct the oligomerization process to produce the oligomer(s) as known and applied in the art and discussed more below.

In a class of embodiments, the feedstream may comprise 30 wt % or more olefins, alternatively, 40 wt % or more olefins, alternatively, 50 wt % or more olefins, alternatively, 60 wt % or more olefins, alternatively, 70 wt % or more olefins, and alternatively, 80 wt % or more olefins, based upon the total weight of the feed. The olefins to be oligomerized may be one or more of $C_3$-$C_{15}$ olefins or mixtures thereof including one or more paraffins having the same or different carbon number, alternatively, $C_3$-$C_6$ olefins or mixtures thereof including one or more paraffins having the same or different carbon number, and alternatively, $C_3$-$C_5$ olefins or mixtures thereof including one or more paraffins having the same or different carbon number.

In any of the embodiments described herein, the feedstream may be free of aromatic hydrocarbon compounds that consist solely of hydrogen and carbon or be substantially free of aromatic hydrocarbon compounds that consist solely of hydrogen and carbon. As used herein, "substantially free" refers to 25 wt % or less of the aromatic hydrocarbon compound present in the feedstream(s), alternatively, 15 wt % or less, alternatively, 10 wt % or less, alternatively, 5 wt % or less, and alternatively, 1 wt % or less, based upon the total weight of the feedstream(s).

Additionally, the feedstream may comprise isomers of any of the constituents found therein. As used herein, "isomer" refers to compounds having the same molecular formula but different structural formula. Examples may be structural isomers, stereoisomers, enantiomers, geometrical isomers, etc. Typically, the feedstream may comprise at least one isomer of the olefin(s) or other constituents in the feedstream.

In a class of embodiments, the feedstream may also comprise contaminants or compounds that may hinder catalyst life or productivity. These may include nitrogen, sulfur, chlorine, oxygen containing compounds, and mixtures thereof.

Examples of nitrogen containing compounds include nitriles (for example, acetonitrile, propionitrile, etc.), ammonia, amides, amines, pyridines, imides, cyanates, pyrroles, pyrrolidones, and mixtures thereof.

As used herein, "pyrrole" is any heterocyclic organic nitrogen-containing compound generally comprising a five-membered ring with the formula $C_4H_4NH$. It may also refer to substituted derivatives thereof.

As used herein, "nitrile" is any organic compound that has a nitrile group (or $-C\equiv N$ functional group). In the nitrile group, the carbon atom and the nitrogen atom are triple bonded together. As used herein, "acetonitrile" is the chemical compound with formula $CH_3CN$. This colorless liquid is the simplest organic nitrile. As used herein, "propanenitrile", "propionitrile", or "ethyl cyanide" is a nitrile with the molecular formula $C_2H_5CN$ and the terms may be used interchangeably. It is also clear liquid. As used herein, "nitrile" may also refer to heavier nitriles. As used herein, "pyrrole" is a heterocyclic aromatic organic compound, a five-membered ring with the formula $C_4H_4NH$. Substituted derivatives may also be referred to as pyrroles.

In a class of embodiments, the nitrogen content in the feedstream before solvent extraction processing may be about 3.00 ppm or more, alternatively, 1.50 ppm or more, alternatively, 10 ppm or more, alternatively, 20 ppm or more, and alternatively, 30 ppm or more, calculated on an atomic basis by weight (wt ppm) when indicated.

In a class of embodiments, the nitrogen content in the feedstream after solvent extraction processing may be about 1.50 ppm or less, alternatively, 1.00 ppm or less, alternatively, 0.50 ppm or less, alternatively, 0.30 ppm or less, 0.20 ppm or less, and alternatively, 0.10 ppm or less calculated on an atomic basis by weight (wt ppm) when indicated.

Examples of sulfur containing compounds include mercaptans such as, for example, methyl mercaptan, ethyl mercaptan, propyl mercaptan, sulfides, such as, for example, dimethyl sulfide, diethyl sulfide, ethyl methyl sulfide, n-propyl sulfide, 1-propane thiol, 2-propane thiol, 1-butane thiol, 1,1-methylethyl thiol, ethylmethyl disulfide, dimethyl disulfide, tetrahydrothiopene, carbonyl sulfide, carbon disulfide and mixtures thereof.

In a class of embodiments, the sulfur content in the feedstream before solvent extraction processing may be about 1.50 ppm or more, alternatively, 10 ppm or more, alternatively, 20 ppm or more, and alternatively, 30 ppm or more calculated on an atomic basis by weight (wt ppm) when indicated.

In a class of embodiments, the sulfur content in the feedstream after solvent extraction processing may be about 3.00 ppm or less, alternatively, 2.50 ppm or less, alternatively, 2.00 ppm or less, alternatively, 1.50 ppm or less, alternatively, 1.00 ppm or less, 0.50 ppm or less, alternatively, 0.30 ppm or less, 0.20 ppm or less, and alternatively, 0.10 ppm or less, calculated on an atomic basis by weight (wt ppm) when indicated.

In a class of embodiments, the feedstream may also comprise other compounds that may hinder catalyst life or productivity. These may include linear and cyclic dienes such as butadiene, pentadiene, cyclo pentadiene, and mixtures thereof.

Solvent extraction processing may refer to one or more extractions of the same or different solvent extraction process taking into account variations in the materials and methodology. Thus, the levels of nitrogen and sulfur in the feedstreams referred to above may be obtained after one or more solvent extraction processes.

Examples of suitable feedstreams include untreated refinery streams such as Fluidized Catalytic Cracking (FCC), coker, and pygas streams as well as aromatics-containing streams, such as, for example, reformates.

Other examples include Raffinate-1 (RAF-1) and/or Raffinate-2 (RAF-2). Typically, Raffinate-1 and Raffinate-2 may be regarded as stages in the processing of crude, generally, $C_4$ streams. These streams are usually from olefin steam crackers but may also come from refinery cat-crackers in which case they generally contain the same components but in different proportions. The first stage of the process is to remove, by generally solvent extraction or hydrogenation, the butadiene which may be 40-45% of the stream. The remaining product is Raffinate-1. It generally consists of isobutylene, the two normal isomers, butene-1 and butene-2, and smaller quantities of butanes and other compounds. Removal of the isobutylene, usually by reaction with methanol to produce MTBE, leaves Raffinate-2. Raffinate 3 (RAF-3) is less common but may also be used. Raffinate 3 may be obtained after separation of 1-butene from Raffinate 2 with a residual 1-butene content of about 1%.

In a class of embodiments, the density at 15° C. (typically as measured by ASTM D4052 unless otherwise noted) of liquid olefin oligimerization feed under pressure varies depending on the composition. For example, a predominately pressurized $C_3$ containing feed may typically have a liquid density at 15° C. of from 0.48 to 0.52 kg/l, a predominately pressurized $C_4$ containing feed may typically have a liquid density at 15° C. of from 0.54 to 0.61 kg/l, a predominately $C_5$ containing feed may typically have a liquid density at 15° C. of from 0.60 to 0.66 kg/l, a mixed pressurized $C_4$ and $C_5$ liquid olefin oligimerization feed may typically have a liquid density at 15° C. of from 0.58 to 0.65 kg/l, and a mixed pressurized $C_3$ and $C_5$ liquid olefin oligimerization feed may typically have a liquid density at 15° C. of from 0.50 to 0.65 kg/l.

By comparison, density of other petroleum type streams are substantially different. Typical petroleum distillate products (e.g., gas oil, diesel, heating oil, etc.) may have a liquid density at 15° C. of 0.82 kg/l or more, fuel oil may have a liquid density at 15° C. typically of 0.90 kg/l or more. Raw crude or shale oil as processed in refineries may have a liquid density at 15° C. typically of 0.79 kg/l or more. Other related products like coal tar may have a liquid density at 15° C. typically of 0.95 kg/l or more.

Thus, in several classes of embodiments disclosed herein, the feedstreams may have liquid densities at 15° C. (in accordance with ASTM D4052) of from 0.45 to 0.70 kg/l, alternatively, from 0.50 to 0.66 kg/l, and alternatively, from 0.54 to 0.65 kg/l. In other embodiments, the feedstreams may have liquid densities at 15° C. (in accordance with ASTM D4052) of 0.94 kg/l or less, alternatively, of 0.89 kg/l or less, and alternatively, of 0.78 kg/l or less.

In another embodiment, the feedstream comprises an FCC light olefin stream that typically comprises ethane, ethylene, propane, propylene, isobutane, n-butane, butenes, pentanes, and other optional components. A specific example of such a feedstream may comprise the following:

|  | Wt % | Mol % |
| --- | --- | --- |
| Ethane | 3.3 | 5.1 |
| Ethylene | 0.7 | 1.2 |

| | Wt % | Mol % |
|---|---|---|
| Propane | 4.5 | 15.3 |
| Propylene | 42.5 | 46.8 |
| Isobutane | 12.9 | 10.3 |
| n-Butane | 3.3 | 2.6 |
| Butenes | 22.1 | 18.32 |
| Pentanes | 0.7 | 0.4 |

In several classes of embodiments the feedstream(s) may comprise a diluent. The diluent may comprise any suitable hydrocarbon such as alkanes or a mixture comprising at least one alkane. The alkanes may be represented the general formula: $C_nH_{2n+2}$, wherein n is a number from 1 to 20, alternatively, from 1 to 10, alternatively, from 1 to 5, and alternatively, from 3 to 4. Examples may include methane, ethane, propane, butane, pentane, and mixtures thereof. In a class of embodiments and when the diluent is present, the feedstream(s) may comprise at least 10%, at least 25%, at least 30%, at least 35%, or at least 40% of the diluent, for example, the alkane such as propane and/or butane, based upon the total volume of the feedstream. Alternatively stated, the diluent may be present in the feedstream in the range from 10% to 40%, alternatively, from 10% to 35%, and alternatively, from 20% to 35% based upon the total volume of the feedstream. The diluent may also be delivered to the reactor(s) through separate feedstreams. When fed separately, the diluent may be fed in amounts to be equivalent to the embodiments wherein the diluent is co-fed with the feedstream. These amounts may not necessarily be the same as the ranges stated above given that more or less of the diluent may be necessary when fed separately to provide an equivalent. In some embodiments, the diluent, when present, may improve reactor continuity.

Additionally, the feedstream may undergo further processing and purification steps prior to being introduced into the oligomerization reactor(s). For example, further processing may include hydrogenation (e.g., using a supported palladium catalyst) to remove or reduce the concentrations of dienes and/or distillation to reduce the level saturated hydrocarbons.

In several classes of embodiments and prior to oligomerization, the feedstream may also be hydrated (i.e., contacted with water) and in an embodiment sufficient water may be added to saturate the feedstream. In particular, the feedstream may comprise from about 0.01 to about 0.25, alternatively, from about 0.02 to about 0.20, and alternatively, from about 0.03 to about 0.10, mol % water based on the total hydrocarbon content of the feedstream. If desired and by way of example, the water content of the feedstream may be increased by passage through a thermostatted water saturator.

The reaction system may include one or more of a fixed bed reactor, a packed bed reactor, a tubular reactor, a fluidized bed reactor, a slurry reactor, a continuous catalyst regeneration reactor, and any combination thereof. They may be operated in any combination such as, for example, in series and/or parallel sequence. In several embodiments, they may be operated in semi-continuous (i.e., continuous but down for routine maintenance), continuous, or batch mode.

The oligomerization conditions may include operating temperatures from about 80° C. to about 350° C. Close to and above the upper end of the range, deoligomerization rates increase and may predominate over the oligomerization reaction providing an upper limit to practical operation. More typically, the reaction temperature is from about 130° C. to about 320° C., alternatively, from about 135° C. to about 310° C., and alternatively, from about 160° C. to about 270° C.

The pressure may be in the range of from about 400 psig to about 4000 psig (2860 to 27680 kPa), and alternatively, from about 500 psig to about 1500 psig (3550 to 10440 kPa).

The olefin weight hourly space velocity may be in the range of from about 0.1 hr−1 to about 20 hr−1 or from about 0.5 hr−1 to about 5 hr−1.

In one embodiment, the process is conducted at a temperature of 80-350° C.; an olefin weight hourly space velocity of 0.1-20 hr−1; and a pressure of 2860-27680 kPa.

In another embodiment, the process is conducted at a temperature of 130-320° C.; an olefin weight hourly space velocity of 0.5-5 hr−1; and a pressure of 3550-10440 kPa.

One or more catalysts may be used in the oligomerization processes of several embodiments of the invention. Any catalyst may be used so long as it is suitable to oligomerize olefins. Both homogeneous and heterogeneous catalysts may be used. For heterogeneous catalysts, they are generally divided into crystalline and amorphous (non-crystalline) catalyst categories. Crystalline catalysts include, without limitation, molecular sieve catalysts such as, for example, zeolite catalysts, in particular, H-zeolites. Non-crystalline catalysts include, without limitation, solid acid catalysts such as, for example, solid phosphoric acid catalyst (sPa) and supported metal catalysts or supported metal oxide catalysts. Commercial processes include the CATPOLY™ Process (UOP and Sud Chemie) employing phosphoric acid on a silica support. One example of a process that utilizes a solid phosphoric acid oligomerization catalyst is disclosed in U.S. Pat. No. 6,025,533, which describes a process for the production of heavy oligomers by a combination of dehydrogenation and oligomerization. See also the disclosure and examples in European Patent Nos. EP570411B and EP1694617B. The OCTOL™ Process (UOP/Huels (now Evonik)) employing a nickel containing catalyst on a silica/alumina support is also useful. See *Make plasticizer olefins via n-butene dimerization* R. H. Friedlander et al., Hydrocarbon Processing, February 1986, pages 31-33, and U.S. Pat. No. 5,177,282. Amorphous silica alumina supports are useful and commonly utilized. Solid acid catalysts may be optionally practiced with promoters such as $TaF_5$.

In another embodiment, an example includes the IFP (now Axens) DIMERSOL processes which employ a Ni-based homogeneous catalyst. (See, for example, Y. Chauvin et al., Chemistry and Industry, 1974, pages 373-378 and U.S. Pat. No. 3,655,810.) Additionally, U.S. Pat. No. 4,225,743 discloses a homogeneous catalyst system consisting of a nickel (II) salt of octanoic acid, ethylaluminium dichloride, and a free fatty acid.

In a class of embodiments, the oligomer product may include a hydrocarbon composition comprising at least 80 wt %, alternatively, at least 90 wt % based upon the total weight of the reactor effluent (the final reactor effluent if one or more reactors are utilized) of $C_6$ to $C_{20-}$ olefin or a mixture thereof.

The oligomer product is useful in many applications and is the starting material for further hydroprocesses. For example, the oligomer product may be polymerized to produce polyolefins that have application in the plastic industry and synthetic basestocks for lubricants. The oligomer product may undergo hydroformylation and subsequently hydrogenation to produce alcohols. The alcohols may be used in industry such as, for example, solvents, or be incorporated into the production of detergents/surfactants.

The alcohols may further be used in many other areas of industry such as, for example, undergoing esterification to produce esters that have application as plasticizers. The oligomer product may also be a blend component for fuels.

Catalyst Life

As used herein, "catalyst life" (Tpdt/Tcat) describes the number of tons of product produced per ton of formulated catalyst. It may be plotted against a setpoint temperature at a given space velocity and at a given olefin conversion rate.

In a class of embodiments, inventive oligomerization processes provide for a longer catalyst life (for example, as represented by Tpdt/Tcat) at a desirable conversion. For example, embodiments utilizing feedstream(s) that have undergone solvent extraction processing may enjoy 10% or greater, alternatively, 20% or greater, alternatively, 30% or greater, alternatively, 40% or greater, alternatively, 50% or greater, alternatively, 75% or greater, alternatively, 100% or greater, alternatively, 150% or greater, and alternatively, 200% or greater, at oligomerization temperatures of from 180° C. to 320° C., alternatively, 210° C. to 300° C., alternatively, 210° C. to 250° C., and alternatively, 210° C. to 240° C., at an olefin constant conversion rate of from 60 to 99 wt % based upon the total weight of olefins, alternatively, from 70 to 95 wt %, alternatively, from 75 to 99 wt %, alternatively, from 75 to 95 wt %, and alternatively, at about 75 wt %, as opposed to oligomerization processes and feedstream(s) that have not undergone solvent extraction processing. The space velocity for the aforementioned embodiments may be in the range of 1 to 20 $h^{-1}$. In an embodiment, the space velocity is 12 $h^{-1}$.

Regeneration and Recycle

Ideally in several embodiments, the at least one solvent will be highly stable and be capable of being reused or recycled in the extraction process but generally requiring some treatment or regeneration. Methods to remove undesired materials from the at least one solvent after use in extraction processes include, but are not limited to, vacuum and steam distillation, back extraction, adsorption (e.g., using a solid adsorbent), and anion-cation exchange resin columns.

Regeneration may also include contacting the at least one solvent after use in extraction processes with an inert gas such as, for example, helium, nitrogen, etc., or one or more of the Group 15-18 inert gases. As used herein, all reference to the Periodic Table of the Elements and groups thereof is to the NEW NOTATION published in HAWLEY'S CONDENSED CHEMICAL DICTIONARY, Thirteenth Edition, John Wiley & Sons, Inc., (1997) (reproduced there with permission from IUPAC), unless reference is made to the Previous IUPAC form denoted with Roman numerals (also appearing in the same), or unless otherwise noted. In a class of embodiments, hot stripping is used to regenerate the at least one solvent after use in extraction processes, for example, hot nitrogen stripping.

Additionally, regeneration may also include contacting the at least one solvent after use in extraction process with a "light" hydrocarbon (as defined above) such as one or more of an alkane (as defined above) having twenty or less carbon atoms, alternatively, ten or less carbon atoms, e.g., propane or a mixture comprising propane.

Methods and equipment of regeneration are known in the art and may vary in their application including combining any suitable material and method to regenerate the at least one solvent after use in extraction processes.

EXAMPLES

It is to be understood that while the invention has been described in conjunction with the specific embodiments thereof, the foregoing description is intended to illustrate and not limit the scope of the invention. Other aspects, advantages and modifications will be apparent to those skilled in the art to which the invention pertains.

Therefore, the following examples are put forth so as to provide those skilled in the art with a complete disclosure and description and are not intended to limit the scope of that which the inventors regard as their invention.

Example 1

A $C_5$ sample feedstream was extracted at room temperature with propylene carbonate, by manual shaking for 1 min in a separation funnel with a propylene carbonate/$C_5$ weight ratio of 0.35. After the two phases had settled, they were separated and analyzed for nitrogen using a Gas Chromatograph equipped with a nitrogen chemoluminescence detector sensitive to nitrogen species only. A WCOT fused silica column of 30 mtr×0.32 mm ID with a CP-Sil 8CB coating was used (Varian CP7596).

The $C_5$ sample analyzed had the following composition.

TABLE 1

| Feedstream | Wt % |
| --- | --- |
| iso-pentane | 28.6 |
| n-pentane | 4.5 |
| iso-pentenes | 29.8 |
| n-pentenes | 22.3 |
| cyclopentene | 2.3 |
| $C_5$ dienes | 1.5 |
| hexenes | 4.5 |
| hexanes | 5.2 |
| $C_7$+ | 1.3 |

The propionitrile concentration in this $C_5$ sample was 8.8 wt ppm N, equivalent to 34.5 ppm propionitrile.

The distribution coefficient determined in this example is:

$$\text{distribution-coefficient} = \frac{molPCN/l_{C5}}{molPCN/l_{PC}} = 0.06$$

wherein $molPCN/l_{C5}$ is the molar concentration of propionitrile in the $C_5$ sample after extraction and $molPCN/l_{PC}$ is the molar concentration of propionitrile in propylene carbonate after extraction.

Example 2

A $C_5$ sample feedstream was extracted at room temperature with propylene carbonate, by manual shaking for 1 min in a separation funnel with a propylene carbonate/C5 weight ratio of 0.08. After the two phases had settled, they were separated and analyzed for nitrogen using a Gas Chromatograph equipped with a nitrogen chemoluminescence detector sensitive to nitrogen species only. A WCOT fused silica column of 30 mtr×0.32 mm ID with a CP-Sil 8CB coating was used (Varian CP7596).

The $C_5$ sample analyzed had the following composition.

TABLE 2

| Feedstream | Wt % |
| --- | --- |
| iso-pentane | 28.6 |
| n-pentane | 4.5 |

TABLE 2-continued

| Feedstream | Wt % |
|---|---|
| iso-pentenes | 29.8 |
| n-pentenes | 22.3 |
| cyclopentene | 2.3 |
| $C_5$ dienes | 1.5 |
| hexenes | 4.5 |
| hexanes | 5.2 |
| $C_7$+ | 1.3 |

The propionitrile concentration in this $C_5$ Sample was 9.0 wt ppm N, equivalent to 35.6 ppm propionitrile.

The distribution coefficient determined in this example is:

$$\text{distribution-coefficient} = \frac{molPCN/l_{C5}}{molPCN/l_{PC}} = 0.05$$

wherein $molPCN/l_{C5}$ is the molar concentration of propionitrile in the $C_5$ sample after extraction and $molPCN/l_{PC}$ is the molar concentration of propionitrile in propylene carbonate after extraction.

Example 3

A $C_5$ sample feedstream was extracted at room temperature with propylene carbonate, by manual shaking for 1 min in a separation funnel with a propylene carbonate/C5 weight ratio of 0.08. After the two phases had settled, they were separated and analyzed for nitrogen using a Gas Chromatograph equipped with a nitrogen chemoluminescence detector sensitive to nitrogen species only. A WCOT fused silica column of 30 mtr×0.32 mm ID with a CP-Sil 8CB coating was used (Varian CP7596).

The $C_5$ sample used had the following composition.

TABLE 3

| Feedstream | Wt % |
|---|---|
| iso-pentane | 28.6 |
| n-pentane | 4.5 |
| iso-pentenes | 29.8 |
| n-pentenes | 22.3 |
| cyclopentene | 2.3 |
| $C_5$ dienes | 1.5 |
| hexenes | 4.5 |
| hexanes | 5.2 |
| $C_7$+ | 1.3 |

The propionitrile concentration in this $C_5$ Sample was 10.4 wt ppm N, equivalent to 41.0 ppm propionitrile.

The distribution coefficient determined in this example is:

$$\text{distribution-coefficient} = \frac{molPCN/l_{C5}}{molPCN/l_{PC}} = 0.05$$

wherein $molPCN/l_{C5}$ is the molar concentration of propionitrile in the $C_5$ sample after extraction and $molPCN/l_{PC}$ is the molar concentration of propionitrile in propylene carbonate after extraction.

Example 4

A $C_5$ sample feedstream was extracted at room temperature with sulfolane, by manual shaking for 1 min in a separation funnel with a sulfolane/C5 weight ratio of 0.22. After the two phases had settled, they were separated and analyzed for nitrogen using a Gas Chromatograph equipped with a nitrogen chemoluminescence detector sensitive to nitrogen species only. A WCOT fused silica column of 30 mtr×0.32 mm ID with a CP-Sil 8CB coating was used (Varian CP7596).

The $C_5$ sample used had the following composition.

TABLE 4

| Feedstream | Wt % |
|---|---|
| iso-pentane | 28.6 |
| n-pentane | 4.5 |
| iso-pentenes | 29.8 |
| n-pentenes | 22.3 |
| cyclopentene | 2.3 |
| $C_5$ dienes | 1.5 |
| hexenes | 4.5 |
| hexanes | 5.2 |
| $C_7$+ | 1.3 |

The propionitrile concentration in this $C_5$ Sample was 8.5 wt ppm N, equivalent to 33.5 ppm propionitrile.

The distribution coefficient determined in this example is:

$$\text{distribution-coefficient} = \frac{molPCN/l_{C5}}{molPCN/l_{PSulf}} = 0.05$$

wherein $molPCN/l_{C5}$ is the molar concentration of propionitrile in the $C_5$ sample after extraction and $molPCN/l_{Sulf}$ is the molar concentration of propionitrile in sulfolane after extraction.

Example 5

A $C_5$ sample feed stream was extracted at room temperature with (i) water, (ii) ethylene glycol, (iii) tri-ethylene glycol, and (iv) propylene carbonate, by manual shaking for 1 min in a separation funnel with an extractant/feed volume ratio of 1. After the two phases had settled, they were separated and analyzed for nitrogen using a Gas Chromatograph equipped with a nitrogen chemoluminescence detector sensitive to nitrogen species only. A WCOT fused silica column of 30 mtr×0.32 mm ID with a CP-Sil 8CB coating was used (Varian CP7596).

The $C_5$ sample used had the following composition.

TABLE 5

| Feedstream | Wt % |
|---|---|
| iso-pentane | 35 |
| iso-pentene | 35 |
| i-pentene | 30 |

The propionitrile concentration in this $C_5$ sample was 21.7 wt ppm N, equivalent to 85.3 ppm propionitrile.

The distribution coefficients determined in this example are given in Table 6.

TABLE 6

| Solvent | Distribution Coefficient (D) |
|---|---|
| water | 0.36 |
| ethylene glycol | 0.48 |

TABLE 6-continued

| Solvent | Distribution Coefficient (D) |
|---|---|
| tri-ethylene glycol | 0.31 |
| propylene carbonate | 0.11 |

Example 6

A $C_5$ sample feed stream was 4 times extracted at room temperature with (i) water and (ii) propylene carbonate, by manual shaking for 1 min in a separation funnel with an extractant/feed weight of 0.5. After the two phases had settled, they were separated and analyzed for nitrogen using a Gas Chromatograph equipped with a nitrogen chemoluminescence detector sensitive to nitrogen species only. A WCOT fused silica column of 30 mtr×0.32 mm ID with a CP-Sil 8CB coating was used (Varian CP7596).

The $C_5$ sample used had the following composition.

TABLE 7

| | Wt % | Wt PPM |
|---|---|---|
| iso-pentane | 35 | — |
| iso-pentene | 35 | — |
| 1-pentene | 30 | — |
| acetonitrile | — | 4.9 |
| propionitrile | — | 49.1 |
| pyrrole | — | 18.0 |

The concentrations in weight ppm of the nitrogen compounds in the extracted $C_5$ feed are given in Table 8.

TABLE 8

| | Nitrogen Compound | Propylene Carbonate |
|---|---|---|
| acetonitrile | 0 | 0 |
| propionitrile | 4.5 | 0.5 |
| pyrrole | 3.8 | 0 |

The phrases, unless otherwise specified, "consists essentially of" and "consisting essentially of" do not exclude the presence of other steps, elements, or materials, whether or not, specifically mentioned in this specification, so long as such steps, elements, or materials, do not affect the basic and novel characteristics of the invention, additionally, they do not exclude impurities and variances normally associated with the elements and materials used.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited. Additionally, within a range includes every point or individual value between its end points even though not explicitly recited. Thus, every point or individual value may serve as its own lower or upper limit combined with any other point or individual value or any other lower or upper limit, to recite a range not explicitly recited.

All priority documents are herein fully incorporated by reference for all jurisdictions in which such incorporation is permitted and to the extent such disclosure is consistent with the description of the present invention. Further, all documents and references cited herein, including testing procedures, publications, patents, journal articles, etc., are herein fully incorporated by reference for all jurisdictions in which such incorporation is permitted and to the extent such disclosure is consistent with the description of the present invention.

While the invention has been described with respect to a number of embodiments and examples, those skilled in the art, having benefit of this disclosure, will appreciate that other embodiments can be devised which do not depart from the scope and spirit of the invention as disclosed herein.

What is claimed is:

1. A process for removing nitriles and/or pyrroles from a feedstream, the process comprising the steps of:
   (a) contacting at least one solvent with one or more adsorbents to remove contaminants of nitrogen and sulfur; and
   (b) contacting at least one feedstream comprising olefins, paraffins, and at least one of a nitrile and/or a pyrrole with the at least one solvent produced in step (a) to remove at least a portion of the nitrile and/or the pyrrole from the at least one feedstream to produce at least one treated feedstream which comprises less than 0.1 ppm of nitrogen and a contaminated solvent;
   (c) regenerating the contaminated solvent produced in step (b) by contacting the contaminated solvent with an inert gas to remove at least a portion of the nitrile and/or pyrrole to produce a regenerated solvent; and
   (d) recycling at least a portion of the regenerated solvent produced in step (c) to step (a).

2. The process of claim 1, wherein the at least one solvent is selected from the group consisting of at least one of alkyl/alkenyl/aryl carbonate, sulfolane, water, a glycol, and mixtures thereof.

3. The process of claim 1, wherein the at least one solvent comprises a compound represented by the formula:

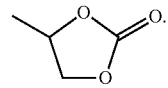

4. The process of claim 1, wherein the at least one feedstream comprises one or more of $C_3$-$C_{15}$ olefins, one or more paraffins having the same or different carbon number, and any isomer thereof.

5. The process of claim 1, wherein the at least one feedstream has a liquid density (in accordance with ASTM D4052) at 15° C. of 0.89 kg/l or less.

6. The process of claim 1, wherein the at least one feedstream has a liquid density (in accordance with ASTM D4052) at 15° C. of 0.78 kg/l or less.

7. The process of claim 1, wherein the nitrile is selected from the group consisting of at least one of acetonitrile, propionitrile, and mixtures thereof.

8. The process of claim 1, wherein the nitrile is propionitrile.

9. The process of claim 1, wherein the process further comprises independently one or more hydrogenation steps and/or distillation steps of the at least one feedstream before or after the contacting of the at least one feedstream with the at least one solvent.

10. The process of claim 1, wherein the process is performed in the temperature range from −25° C. to 75° C.

11. The process of claim 1, wherein the process is performed in the temperature range from −15° C. to 50° C.

12. The process of claim 1, wherein the process further comprises removing at least one of ammonia, amides, amines, pyridines, imides, cyanates, pyrrolidones, and mixtures thereof.

13. The process of claim 1, wherein the process further comprises removing at least one of mercaptans, sulfides, and mixtures thereof.

14. The process of claim 1, wherein the process occurs in a counter-current mode.

15. A process for the oligomerization of olefins, the process comprising the steps of:
(a) contacting at least one solvent with one or more adsorbents to remove contaminants of nitrogen and sulfur;
(b) contacting at least one feedstream comprising olefins, paraffins, and at least one of a nitrile and/or a pyrrole with the at least one solvent produced in step (a) to remove at least a portion of the nitrile and/or the pyrrole from the at least one feedstream to produce at least one treated feedstream which comprises less than 0.1 ppm of nitrogen and a contaminated solvent;
(c) regenerating the contaminated solvent produced in step (b) by contacting the contaminated solvent with an inert gas to remove at least a portion of the nitrile and/or pyrrole to produce a regenerated solvent;
(d) recycling at least a portion of the regenerated solvent produced in step (c) to step (a); and
(e) subsequently contacting the at least one treated feedstream with a catalyst under oligomerization conditions to produce oligomers.

16. The process of claim 15, wherein the at least one feedstream comprises one or more of $C_3$-$C_{15}$ olefins, one or more paraffins having the same or different carbon number, and any isomer thereof.

17. The process of claim 15, wherein the catalyst is selected from the group consisting of at least one of molecular sieve catalysts, solid phosphoric acid catalysts (sPa), metal oxide catalysts, nickel-based homogeneous catalysts, and mixtures thereof.

18. The process of claim 15, wherein the catalyst is a zeolite catalyst.

19. The process of claim 15, wherein the at least one solvent is selected from the group consisting of at least one of an alkyl/alkenyl/aryl carbonate, sulfolane, water, a glycol, and mixtures thereof.

20. The process of claim 15, wherein the adsorbent is selected from the group consisting of molecular sieves, activated carbons, silica gels, resins, and mixtures thereof.

21. The process of claim 15, wherein the inert gas comprises helium, nitrogen or a mixture thereof.

22. The process of claim 15, wherein the contaminated solvent is regenerated by stripping with hot nitrogen.

23. The process of claim 1, wherein the adsorbent is selected from the group consisting of molecular sieves, activated carbons, silica gels, resins, and mixtures thereof.

24. The process of claim 1, wherein the inert gas comprises helium, nitrogen or a mixture thereof.

25. The process of claim 1, wherein the contaminated solvent is regenerated by stripping with hot nitrogen.

* * * * *